United States Patent [19]

Haugwitz et al.

[11] Patent Number: 5,441,941
[45] Date of Patent: Aug. 15, 1995

[54] 1,2-DIHYDROELLIPTICINES WITH ACTIVITY AGAINST CNS SPECIFIC CANCER

[75] Inventors: Rudiger D. Haugwitz, Bethesda; Venkatachiala L. Narayanan, Gaithersburg, both of Md.; Mark Cushman; Jurjus Jurayj, both of West Lafayette, Ind.

[73] Assignees: The United States of America as represented by the Secretary of DHHS, Washington, D.C.; Purdue Research Foundation, Lafayette, Ind.

[21] Appl. No.: 171,234

[22] Filed: Dec. 21, 1993

Related U.S. Application Data

[62] Division of Ser. No. 956,903, Oct. 2, 1992, Pat. No. 5,272,146.

[51] Int. Cl.$^6$ ............... A61K 31/435; A61K 31/535; C07D 471/04

[52] U.S. Cl. ............... 514/43; 514/232.8; 514/285; 536/27.1; 544/124; 546/70; 546/199

[58] Field of Search ............... 546/70, 199; 514/43, 514/232.8, 285; 536/27.1; 544/124

[56] References Cited

PUBLICATIONS

Auclair, Adv. Exp. Med. Biol, 264 (Antioxid. Ther. Prev. Med.) 317–22 [Abstract from Search Report] (1990).

Buechi, Tatrahedron 15, 167–72 (1961) [CA56:11632e enclosed].

*Primary Examiner*—José G. Dees
*Assistant Examiner*—Joseph M. Conrad, III
*Attorney, Agent, or Firm*—Leydig, Voit & Mayer, Ltd.

[57] ABSTRACT

Certain new 1,2-dihydroellipticine compounds having activity against CNS specific cancer cell lines because of their ease of passage across the blood-brain barrier are disclosed along with formulations and methods for treating CNS cancers employing these compounds.

24 Claims, No Drawings

1,2-DIHYDROELLIPTICINES WITH ACTIVITY AGAINST CNS SPECIFIC CANCER

This is a division of application(s) Ser. No. 07/956,903 filed on Oct. 2, 1992, now U.S. Pat. No. 5,272,146.

TECHNICAL FIELD OF THE INVENTION

The present invention is directed, in general, to methods for treating human cancers and in particular to new compounds which cross the blood brain barrier and retain activity against CNS specific cancer cell lines, to pharmaceutical formulations containing such compounds, and to methods for the treatment of cancer.

BACKGROUND OF THE INVENTION

The development of drugs effective against human cancers has been recognized as a critical need. This is particularly true for cancers attacking the central nervous system (CNS). Development of drugs having activity against CNS specific cancer cell lines which are effective in vivo has been especially difficult due to the inability of many anticancer drugs to penetrate the blood-brain barrier or the blood-cerebrospinal fluid (CSF) barrier.

The blood-brain barrier, existing between the blood and brain fluid, and the blood-CSF barrier, existing between the blood and CSF, prevent many large molecular substances from passing from the blood to the interstitial fluids of the brain and the CSF. Generally, these barriers are highly permeable to water, carbon dioxide, oxygen and lipid soluble substances and slightly permeable to electrolytes.

As recognized, the delivery of drug species to the brain is often seriously limited or inhibited by the functional barrier of the endothelial brain capillary wall deemed the blood-brain barrier, BBB. The barriers separating plasma from the brain and cerebrospinal fluid (CSF) are complex systems involving passive and active transport and subserve a number of important functions. The BBB is, moreover, basically the result of the fact that the endothelial cells in the brain capillaries are joined by continuous, tight intercellular junctions, such that material has to pass through the cells rather than between them in order to move from blood to brain.

Thus, foreign compounds, such as therapeutics, which enter organs other than the central nervous system with ease, may penetrate the CNS slowly or hardly at all. A number of theories concerning the nature of the barrier have been proposed. One theory is that the boundary is essentially a fat-like layer interspersed with small pores, although the BBB is not a simple, anatomically well-defined unitary physical entity. Penetration of such a barrier may occur by several processes: lipid soluble substances may passively penetrate into the cells, while small molecules such as water and urea may pass through the pores.

In addition to the aforementioned simplified physical processes, carrier-mediated and active transport processes act to govern the movement of many molecules through the BBB. Some materials such as glucose and amino acids are transported by an active mechanism, characterized by saturation, bidirectional molecular specificity, bidirectional competitive inhibition and bi-directional countertransport. Fishman, *Am. J. Physiol.*, 206, 836 (1964).

It is also known that the BBB is relatively impermeable to the ionized forms of drugs and other molecules. Drugs which are weak organic electrolytes appear to pass from blood to BBB to reach a steady state ratio characteristic of each molecule according to its pKa and the existence of a normal pH gradient between blood and BBB. It is clear, therefore, that quaternary nitrogen-containing salts, such as pyridinium or ammonium salts, penetrate the BBB only with great difficulty, if at all.

Chemical delivery systems (CDSs) have been used to deliver drugs to particular organs. These CDSs generally require that a biologically inert molecule be covalently attached to a drug, thereby producing a highly lipophilic conjugate which can easily penetrate the blood-brain barrier. Several chemical and/or enzymatic steps are then required to release the active drugs. A principal carrier for such CDSs that are used to cross the blood-brain barrier is the dihydropyridine moiety obtained from $Na_2S_2O_4$ reduction of the appropriately substituted pyridinium salt.

U.S. Pat. No. 4,479,932 relates to certain CDSs that tether the target drug species to a reduced, blood-brain barrier penetrating lipoidal form of a dihydropyridine-pyridinium salt type redox carrier. Oxidation of the dihydropyridine carrier moiety in vivo to the ionic pyridinium salt type drug/carrier entity prevents elimination thereof from the brain, while elimination from the general circulation is accelerated, and subsequent cleavage of the quaternary carrier/drug species results in sustained delivery of the drug in the brain and facile elimination of the carrier moiety.

Pyridocarbazole alkaloids such as ellipticine, i.e., 5, 11-dimethyl-6H-pyrido [4,3-b] carbazole (i.e., R=H in the following general formula) and 9-methoxyellipticine (i.e., R =OCH₃ in the following general formula) are known as alkaloids contained in, for example, Aspidospermina and Ochrosia leaves.

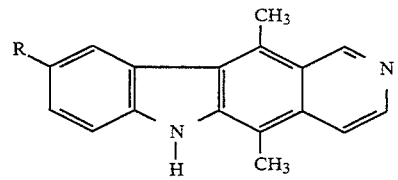

Further, U.S. Pat. No. 4,045,565 discloses that 9-hydroxy-5,11-dimethyl-(6H) -pyrido [4,3-b] carbazole having the following formula:

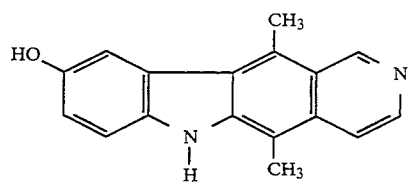

has considerably high antitumor properties with respect to many tumors and particularly mouse L-1210 leukemia.

It has also been reported by J. Rouesse et al., *Bull. Cancer* (Paris), 68, 437–441 (1981) that 2-methyl-9-hydroxyellipticinium acetate (Celiptium) having the formula:

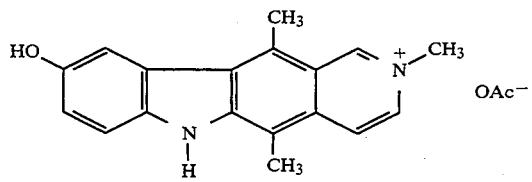

is effective against mammary cancer. It was also reported, by R. W. Guthrie et. al, *J. Medicinal Chemistry*, 18 (7), 755–760 (1975), that ellipticine and 9-methoxyellipticine are effective against the tumor of animals used for experiments, mouse lymphoid leukemia L-1210 and Sarcoma 180 (solid) and, in Japanese Examined Patent Publication (Kokoku) No. 58-35196 and British Pat. No. 1436080, that the activity of 9-hydroxyellipticine against mouse lymphold leukemia L-1210 is higher, by more than 100 to 1000 fold, than that of 9-methoxyellipticine.

Ellipticine compounds have been found to have anti-cancer activity, including elliptinium which exhibits in vitro activity against human glioma lines (SF126, SF375 and SF407), ellipticine glycosides which are active against L1210, P388, B16 melanoma and colon carcinoma in vivo, carbamate which is active against various human lung cancer lines, datelliptium (2-[(2-diethylamino) ethyl]-9-hydroxyellipticinium) which has in vivo activity against L1210, P388, B16, colon and M5076 reticulosarcoma, pazellipticine (PZE) which has in vitro activity against L1210 cells, and oxazolopyridocarbazoles which have antitumor activity in vitro. The mechanism for the antitumor activity of these compounds is unclear. Important factors include metabolic activation of an ellipticine to a quinone imine or related species of high electrophilicity, DNA intercalation, and topoisomerase II as a critical cellular target.

U.S. Pat. No. 4,698,423 also relates to certain quaternary ellipticine derivatives that have antineoplastic or antitumor activity. In accordance with that patented invention, there is provided an ellipticine derivative having the general formula:

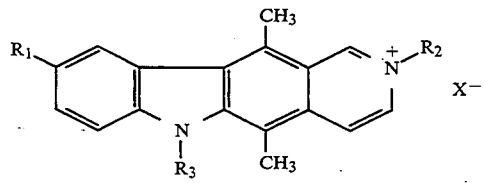

wherein, $R_1$ represents a hydrogen atom, a hydroxyl group, an alkoxyl group having 1 to 4 carbon atoms, or an acyloxy group having 2 to 7 carbon atoms;

$R_2$ represents an aldose residue, a deoxyaldose residue, an N-acylaminoaldose residue, an aldohexuronic amide residue, an aldohexuronic acid residue, an acylated aldose residue, an acylated deoxyaldose residue, an acylated N-acylamino aldose residue, an acylated aldohexuronic amide residue, an acylated aldohexuronic acid residue, an acylated aldohexuronic acid ester residue, an arylalkylated aldose residue, an arylalkylated N-acylaminoaldose residue, an arylalkylated aldohexuronic amide residue, an arylalkylated aldohexuronic acid residue, an arylalkylated aldohexuronic acid ester residue; and $R_3$ represents a hydrogen atom, a linear, branched, cyclic, or cyclic-linear alkyl group having 1 to 5 carbon atoms;

$X^-$ represents a pharmaceutically acceptable inorganic or organic acid anion; and The bond represented by $N^{301}R_2$ in the general formula represents a glycoside bond between a nitrogen atom in the 2-position of the ellipticine and a carbon atom in the 1-position of the sugar.

As disclosed in U.S. Pat. No. 4,310,667, certain specific compounds are known to possess anti-cancer activity, including the water soluble 2-N quaternary salts of the formula:

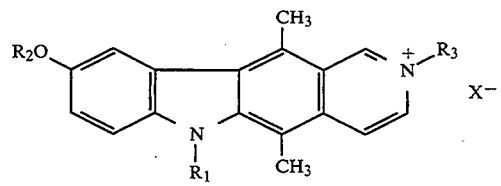

wherein $R_1$ is selected from the groups consisting of hydrogen and alkyl groups; $R_2$ is selected from the groups consisting of hydrogen, alkyl and acyl groups; $R_3$ is an alkyl group; and $X^-$ is an anion.

The problem with the aforementioned ellipticinium derivatives is that the quaternary salt nature of the anti-cancer compounds limits them to only act peripherally because they are unable to cross the blood brain barrier. As a result, these compounds are ineffective against CNS specific cancer cell lines.

A need has therefore existed for compounds and pharmaceutical compositions having activity against CNS specific cancer cell lines which can easily penetrate the blood brain barrier without the need for a separate CDS.

SUMMARY OF THE INVENTION

In accordance with the present invention, it has now been discovered that CNS specific cancers may be effectively treated with certain compounds, as defined in Formula I:

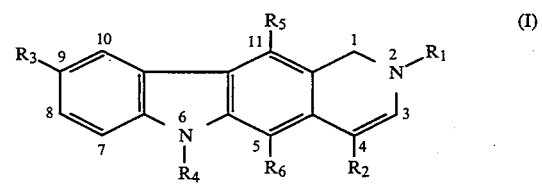

wherein $R_1$ is alkyl having 1 to about 5 carbon atoms, benzyl, alkenyl having 2 to about 5 carbon atoms, alkyloxyalkyl wherein the alkyl portion has 1 to about 5 carbon atoms, hydroxyalkyl having 1 to about 5 carbon atoms, cyanoalkyl having 1 to about 5 carbon atoms, dialkylaminoalkyl wherein each alkyl has 1 to about 5 carbon atoms, glycosyl residue derived from threose, ribose, arabinose, xylose, glucose, mannose, galactose, or acetyl derivatives thereof, acids or alkyl esters selected from the group consisting of $-R_7COOH$ and $-R_7COOR_8$ wherein $R_7$ is an alkyl having 0 to about 4 carbon atoms and $R_8$ is an alkyl having 1 to about 5 carbon atoms; $R_2$ is hydrogen or formyl; $R_3$ is hydrogen, hydroxy, alkyl having 1 to about 5 carbon atoms, alkoxy having 1 to about 5 carbon atoms, phenoxy, benzyloxy, acyloxy, benzoyloxy, fluorine, chlorine, bromine, alkylamino or dialkylamino wherein each alkyl portion has 1 to about 5 carbon atoms or acyloxy having 1 to about 5 carbon atoms; $R_4$ is hydrogen, alkyl having 1 to about 5 carbon atoms, formyl, dialkylaminoalkyl wherein each alkyl portion has 1 to about 5 carbon atoms, morpholino N-alkyl or piperidine N-alkyl, wherein the alkyl has 1 to about 5 carbon atoms; and $R_5$ and $R_6$ are the same or different and are hydrogen or methyl.

Also, there is provided a method of site-specifically treating a CNS cancer, said method comprising administering to an animal in need of such treatment a quantity of a compound as claimed in formula I sufficient to be pharmacologically effective at the site of said cancer. The compound may be administered in any suitable manner, including orally, buccally, sublingually, subcutaneously, intramuscularly, intravenously or rectally.

Further, the present invention provides the aforementioned compounds as formulations for administration to patients for treatment of cancer. Thus, there also is provided a pharmaceutical composition of matter comprising a compound of formula I and a pharmaceutically acceptable carrier therefor. Additionally, the present invention provides a pharmaceutical composition of matter, in unit dosage form, for use as a CNS anticancer agent, said composition comprising:

(i) an amount of a compound as claimed in claim 1 sufficient to release a pharmacologically effective amount of said compound to the brain; and (ii) a pharmaceutically acceptable carrier therefor. The quantity of active agent that is administered will vary widely. For example, the amount may be from about 0.01 to 5 mg per kg of body weight administered 1 to 5 times per day.

Other advantages of the present invention will become apparent from the following detailed description.

DETAILED DESCRIPTION OF THE INVENTION

The 1,2-dihydro compounds of the present invention are described by the general formula, Formula I:

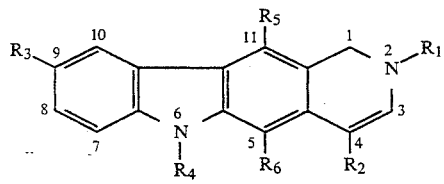

(I)

wherein $R_1$ is alkyl having 1 to about 5 carbon atoms, benzyl, alkenyl having 2 to about 5 carbon atoms, alkyloxyalkyl wherein the alkyl portion has 1 to about 5 carbon atoms, hydroxyalkyl having 1 to about 5 carbon atoms, cyanoalkyl having 1 to about 5 carbon atoms, dialkylaminoalkyl wherein each alkyl has 1 to about 5 carbon atoms, glycosyl residue derived from threose, ribose, arabinose, xylose, glucose, mannose, galactose, or acetyl derivatives thereof, acids or alkyl esters selected from the group consisting of —$R_7COOH$ and —$R_7COOR_8$ wherein $R_7$ is an alkyl having 0 to about 4 carbon atoms and $R_8$ is an alkyl having 1 to about 5 carbon atoms; $R_2$ is hydrogen or formyl; $R_3$ is hydrogen, hydroxy, alkyl having 1 to about 5 carbon atoms, alkoxy having 1 to about 5 carbon atoms, phenoxy, benzyloxy, acyloxy, benzoyloxy, fluorine, chlorine, bromine, alkylamino or dialkylamino wherein each alkyl portion has 1 to about 5 carbon atoms, and each acyloxy has 1 to about 5 carbon atoms; $R_4$ is hydrogen, alkyl having 1 to about 5 carbon atoms, formyl, dialkylaminoalkyl wherein the alkyl portion has 1 to about 5 carbon atoms, morpholino N-alkyl or piperidine N-alkyl, wherein the alkyl has 1 to about 5 carbon atoms; and $R_5$ and $R_6$ are the same or different and are hydrogen or methyl.

When $R_1$ is a glycosyl residue, the glycosyl group may be bound to position 2 of the compound of Formula I in a number of ways. Generally, the glycosyl group is attached by a glycoside bond between the nitrogen atom in the 2-position of the compounds of Formula I and a carbon atom in the 1-position of the glycosyl residue as described in U.S. Pat. No. 4,698,423.

Preferably, the novel compounds have the structures indicated by Formulas II-XXII.

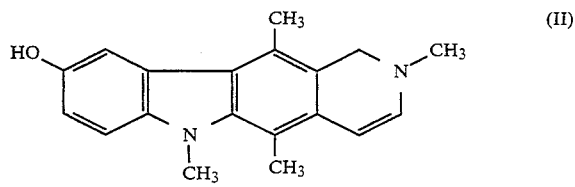

(II)

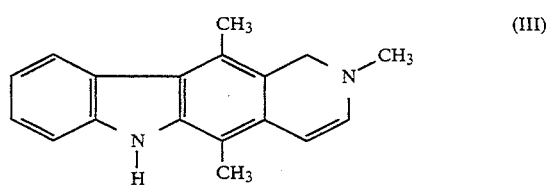

(III)

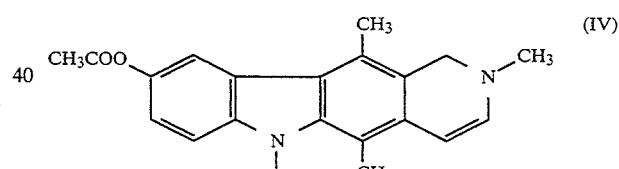

(IV)

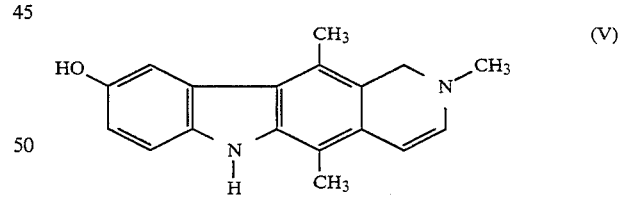

(V)

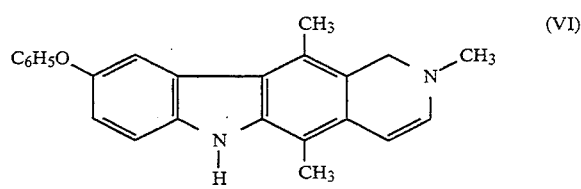

(VI)

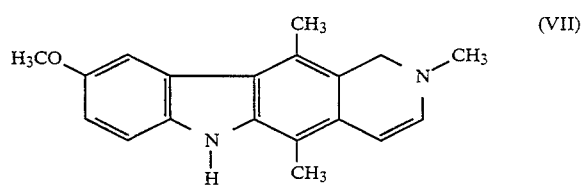

(VII)

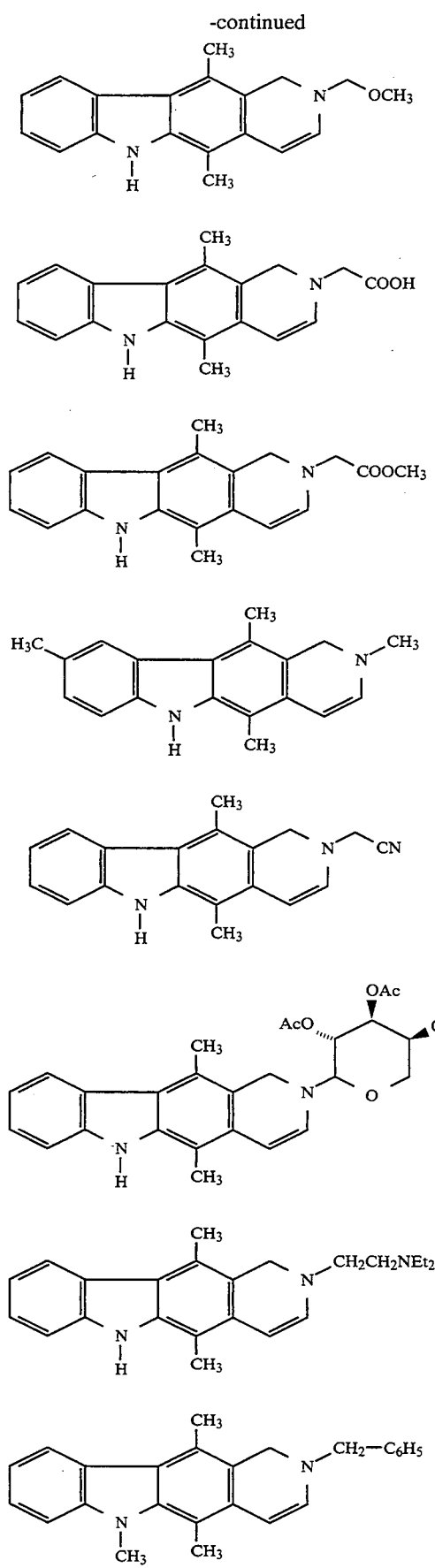
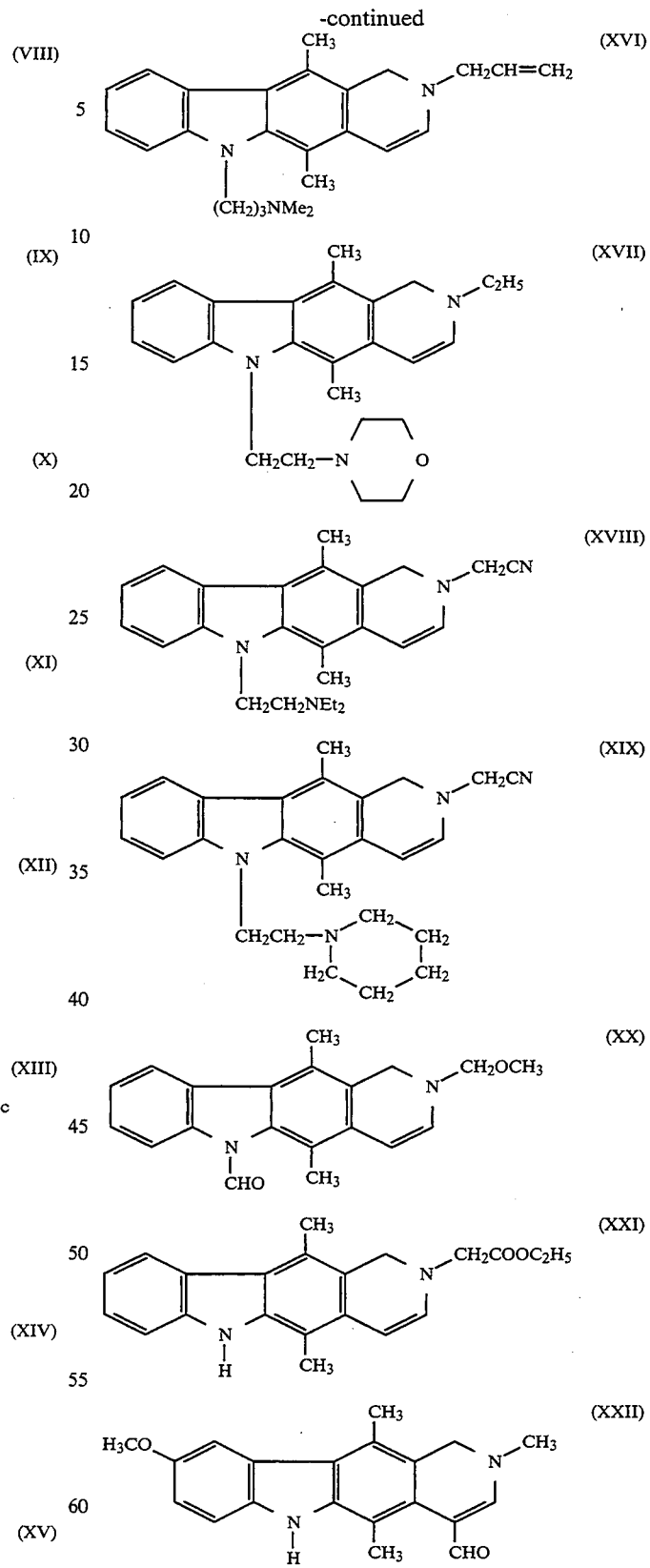
Many of the foregoing compounds are reduced (dihydro) forms of known anti-cancer compounds, specifically certain quaternary ellipticines. Many quaternary ellipticines are known to have good antitumor activity in vivo and in vitro. Generally, such activity is indicative of the compounds' effectiveness against human cancers.

As disclosed in U.S. Pat. No. 4,310,667, certain specific ellipticinium compounds are known to possess anti-cancer activity, including, specifically, the following compounds:

9-hydroxy-2-methyl-ellipticinium acetate,
9-hydroxy-2-ethyl-ellipticinium acetate,
9-hydroxy-2-hydroxyethyl-ellipticinium acetate,
9-hydroxy-2-hydroxypropyl-ellipticinium acetate,
9-hydroxy-2-dihydroxypropyl-ellipticinium acetate,
9-hydroxy-2(beta-diethylamino-ethyl)-ellipticinium acetate,
9-hydroxy-2(beta-diisopropylamino-ethyl)-ellipticinium acetate,
9-hydroxy-2(beta-piperidino-ethyl)-ellipticinium acetate,
9-methoxy-2-methyl-ellipticinium acetate,
9-acetoxy-2-methyl-ellipticinium acetate,
9-acetoxy-2-ethyl-ellipticinium acetate,
9-benzyloxy-2-methyl-ellipticinium acetate,
9-benzyloxy-2-ethyl-ellipticinium acetate,
9-hydroxy-2,6-dimethyl-ellipticinium acetate,
9-hydroxy-6-methyl-2-ethyl-ellipticinium acetate,
9-hydroxy-6-methyl-2-hydroxyethyl-ellipticinium acetate,
9-hydroxy-2,6-diethyl-ellipticinium acetate,
9-hydroxy-6-ethyl-2-hydroxyethyl-ellipticinium acetate,
9-ethoxy-2,6-diethyl-ellipticinium acetate,
9-ethoxy-6-ethyl-2-(beta-hydroxy-ethyl)-ellipticinium acetate,
9-benzoyloxy-2,6-dimethyl-ellipticinium acetate, and
9-benzoyloxy-6-methyl-2-ethyl-ellipticinium acetate, among others.

Further, in accordance with U.S. Pat. No. 4,698,423, as discussed previously, certain other ellipticinium derivatives have also found utility as antitumor and antineoplastic agents.

It has been found that many ellipticinium compounds, such as those of the aforementioned prior art, may be converted to neutral, uncharged species which have been found to be capable of penetrating the blood-brain barrier. Thus the dihydro analogues for any of the aforementioned ellipticinium compounds of the prior art may be made in accordance with the present invention, and the dihydro analogues will possess the desired ability to cross the blood-brain barrier where they may act directly against CNS cancers or may be converted into the corresponding quaternary ellipticinium compound, which will then be active against such cancers.

The compounds employed in the present invention may be synthesized in accordance with procedures generally known and readily understood by those skilled in the art. Neutral, uncharged compounds, for example, may be synthesized by reducing the ionized quaternary ammonium compounds in accordance with the following general reaction sequence:

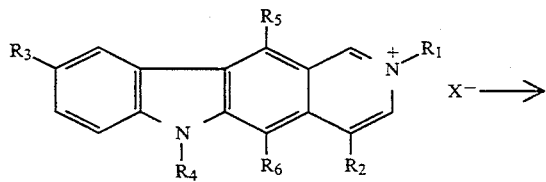

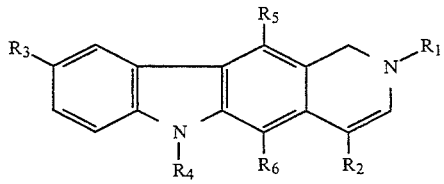

wherein $R_1$ is alkyl having 1 to about 5 carbon atoms, benzyl, alkenyl having 2 to about 5 carbon atoms, alkyloxyalkyl wherein the alkyl portion has 1 to about 5 carbon atoms, hydroxyalkyl having 1 to about 5 carbon atoms, cyanoalkyl having 1 to about 5 carbon atoms, dialkylaminoalkyl wherein each alkyl has 1 to about 5 carbon atoms, glycosyl residue derived from threose, ribose, arabinose, xylose, glucose, mannose, galactose, or acetyl derivatives thereof, acids or alkyl esters selected from the group consisting of —$R_7$COOH and —$R_7$COO$R_8$ wherein $R_7$ is an alkyl having 0 to about 4 carbon atoms and $R_8$ is an alkyl having 1 to about 5 carbon atoms; $R_2$ is hydrogen or formyl; $R_3$ is hydrogen, hydroxy, alkyl having 1 to about 5 carbon atoms, alkoxy having 1 to about 5 carbon atoms, phenoxy, benzyloxy, acyloxy, benzoyloxy, fluorine, chlorine, bromine, alkylamino or dialkylamino wherein each alkyl portion has 1 to about 5 carbon atoms or acyloxy having 1 to about 5 carbon atoms; $R_4$ is hydrogen, alkyl having 1 to about 5 carbon atoms, formyl, dialkylaminoalkyl wherein the alkyl portion has 1 to about 5 carbon atoms, morpholino N-alkyl or piperidine N-alkyl, wherein the alkyl has 1 to about 5 carbon atoms; $R_5$ and $R_6$ are the same or different and are hydrogen or methyl; and wherein $X^-$ in the formula (I) is a pharmaceutically acceptable anion. Preferably, the anion is derived from an inorganic acid selected from the group consisting of hydrochloric acid, sulfuric acid, phosphoric acid, hydroidic acid, hydrobromic acid, and perchloric acid or an anion derived from an organic acid selected from the group consisting of acetic acid, propionic acid, oxalic acid, tartaric acid, lactic acid, malic acid, formic acid, fumaric acid, maleic acid, butyric acid, valeric acid, caproic acid, heptanoic acid, and capric acid.

Lithium aluminum hydride and polymer-supported borohydride are preferred reducing agents for the reduction of ellipticinium derivates. Ethyl ether and tetrahydrofuran are the reaction media of choice for lithium aluminum hydride, while pyridine is preferred for polymer-supported borohydride. Reflux of the reaction medium may be necessary when highly unreactive quarternary salts are involved. Generally, these reactions are run at room temperature.

The 1,2-dihydroellipticines of the present invention may act against CNS specific cancer cell lines in two possible ways. The 1,2-dihydroellipticines may, upon entry into the brain, oxidize in vivo to form the corresponding ionized active species. Alternatively, the 1,2-dihydroellipticines may be directly active against CNS specific cell lines.

The present invention, in one embodiment, thus provides an integral redox system for the delivery of a wide variety of ellipticinium drug species to the brain. In accordance with the present invention, the dihydrocompounds of the present invention penetrate the blood-brain barrier ("BBB") and attain increased levels of concentration in the brain. Oxidation of the dihydrocompounds in vivo once the compounds have crossed the BBB, to the corresponding ionic salts, then decreases the rate of elimination from the brain. The oxidation of the dihydro-compounds in the brain may also act as a rate-limiting step that will inherently provide for a means of controlling the concentration of active compound in the brain. Alternatively, if the compound is immediately oxidized to the corresponding quaternary salt, the elimination rate of that ionic species from the brain should be slowed significantly, analogous to the quaternary salt that is formed in situ after delivery of a haloalkylamine, which undergoes cyclization to the quaternary salt, in the brain, which has been found to have an at least ten times slower elimination rate from the brain than from the rest of the body. Ross and Froden, *Eur, J, pharmacol.*, 13, 46 (1970).

It is speculated that for many of the compounds of the present invention it is not required for them to oxidize to be active. Thus, it is believed that the 1,2-dihydroellipticines of the present invention may be directly active against CNS cancers or tumors, without the need for them to oxidize first.

One especially important aspect of the present invention, is the provision of a method of treating cancer. This method is particularly useful in treating CNS cancers. The present method includes the administration to an animal, particularly a human, of a therapeutically effective amount of a compound of the present invention, capable of crossing the blood-brain barrier and retaining, or oxidizing to obtain, activity against CNS specific cancer cell lines. The use of such a compound in treating animals, particularly humans, circumvents the need for separate chemical delivery systems (CDS) for transporting effective anti-cancer drugs across the blood-brain barrier.

The compounds and method of the present invention are useful against many CNS cancer cell lines, including the following: SF-268, SF-295, SF-539, SNB-19, SNB-95, SNB-78, U-251, XF-4986, SF-126, SF-375, and SF-407.

As regards the in vivo use of the present inventive method, a neutral, uncharged anti-cancer compound capable of crossing the blood-brain barrier in the context of the present invention can be administered in any suitable manner, preferably with pharmaceutically acceptable carriers. The attenuation of tumor cell proliferation in an animal has utility in, for example, the in vivo treatment of cancerous cells.

One skilled in the art will appreciate that suitable methods of administering neutral, uncharged anti-cancer compounds capable of crossing the blood-brain barrier in the context of the present invention to an animal are available, and, although more than one route can be used to administer a particular compound, a particular route can provide a more immediate and more effective reaction than another route. Pharmaceutically acceptable carriers are also well-known to those who are skilled in the art. The choice of carrier will be determined in part by the particular compound, as well as by the particular method used to administer the composition. Accordingly, there is a wide variety of suitable formulations of the pharmaceutical composition of the present invention.

Suitable specific forms of administration include the forms for the oral route, buccal and sublingual forms of administration, subcutaneous, intramuscular or intravenous forms of administration and rectal forms of administration. For topical application, the compounds according to the invention may be used in creams, ointments or lotions.

The pharmaceutical compositions of the present invention for oral, buccal, nasal, sublingual, subcutaneous, intramuscular, intravenous, topical, transdermal or rectal administration, the active ingredients, may be administered in dosage unit forms of administration mixed with standard pharmaceutical vehicles to animals or humans for the prophylaxis or treatment. The formulations may conveniently be prepared by any of the methods well known in the art.

Formulations suitable for oral administration can consist of (a) liquid solutions, such as an effective amount of the compound dissolved in diluents, such as water or saline, (b) capsules, sachets or tablets, each containing a predetermined amount of the active ingredient, as solids or granules, (c) suspensions in an appropriate liquid, and (d) suitable emulsions. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use.

Extracorpeal injection solutions and suspensions can be prepared from sterile powders, granules, and tablets of the kind previously described. Solution forms may include buffers, such as acetate and phosphate, toxicity adjusting agents, such as sodium chloride, pH adjusting agents, such as HCl and phosphoric acid, bacteriocides, and the like. Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Tablet forms can also include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers.

Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The neutral, uncharged anti-cancer compounds capable of crossing the blood-brain barrier in the context of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

The dose administered to an animal, particularly a human, in the context of the present invention should be sufficient to effect a therapeutic response in the animal over a reasonable time frame. The dose will be determined by the strength of the particular compound employed and the condition of the animal, as well as the body weight of the animal to be treated. The size of the dose also will be determined by the existence, nature, and extent of any adverse side-effects that might accompany the administration of a particular compound.

In the treatment of some individuals with the pharmaceutical composition of the present invention, it may be desirable to utilize a "mega-dosing" regimen. In such a treatment, a large dose of the pharmaceutical composition is administered to an individual, time is allowed for the active compound, i.e., the neutral, uncharged anticancer compound to act, and then a suitable reagent is administered to the individual to render the active compound ineffective.

The desirable extent of the inhibition of cell proliferation rate will depend on the particular condition or disease being treated, as well as the stability of the patient and possible side-effects. In proper doses and with suitable administration of certain compounds, the present invention provides for a wide range of the inhibition of the normal cell proliferation rate, e.g., from little inhibition to essentially full inhibition.

The dose varies, the daily dose being generally 0.1 mg to 500 mg, desirably 1 mg to 30 mg.

The most preferred dosage for extracorporeal administration is in the range from about 0.1 mg/kg to 5 mg/kg of body weight per day. For the oral, rectal, topical (including buccal and sublingual) or transdermal route of administration, the preferred dosage thereof (estimated as the base) is in the range 0.05 mg/kg to 20 mg/kg of body weight: per day.

All patents and publications cited to or referenced herein are incorporated herein by reference, in their entirety.

The present invention will be further illustrated by the following non-limiting examples.

EXAMPLE 1

This Example illustrates the preparation of 9-methoxy-2-methyl-1,2-dihydroellipticine. Lithium aluminum hydride powder (300 mg, 7.95 mmol) was added in one portion to an ice cold suspension of 9-methoxy-2-methylellipticinium acetate (NSC 627505, 200 mg, 0.57 mmol) in anhydrous ether (50 mL). The ice bath was removed and the mixture was stirred under an atmosphere of nitrogen for 18 hours. The reaction mixture was cooled in an ice bath and quenched by the sequential addition of water ( 0.3 mL), 15% aqueous sodium hydroxide (0.3 mL), and water ( 0.9 mL) . The granular aluminum salts thus formed were filtered off and washed with anhydrous ether (20 mL). The filtrate was concentrated on a rotary evaporator to give a greenish yellow solid (151 mg, 91%). This solid was stored either under vacuum or an inert atmosphere: mp 205°–207° C. (dec, determined under vacuum), UV (ethanol) 362 ($\epsilon$=36040), 249 ($\epsilon$=55000); $^1$H NMR (500 MHz, CDCl$_3$) $\delta$7.68 (br, 1H), 7.65 (d, 1 H, J=3 Hz), 7.31 (d, 1 H, J=9 Hz), 6.98 (dd, 1 H, J=9,3 Hz), 6.20 (d, 1 H, J=8 Hz), 5.54 (d, 1 H, J=8 Hz), 4.38 (s, 2 H), 3.92 (s, 3H), 2.84 (s, 3 H), 2.69 (s, 3 H), 2.37 (s, 3H); low resolution CIMS m/e (relative intensity) 293 (MH+, 67) , 292 (M+, 100); high resolution CIMS m/e calcd MH+ 293.1654 found 293.1660.

EXAMPLE 2

This Example illustrates the preparation of 2,9-dimethyl-1,2-dihydroellipticine. Solid lithium aluminum hydride (300 mg, 7.95 mmol) was added at once to an ice cold suspension of 2,9-dimethyellipticinium acetate (NSC D639364, 200 mg, 0.599 mmol) in anhydrous ether (60 mL). The ice bath was removed and the mixture was stirred under an atmosphere of argon for 9 hours. The reaction mixture was cooled in an ice bath and quenched by the sequential addition of water (0.3 mL), 15% aqueous sodium hydroxide (0.3 mL), and water (0.9 mL). The granular aluminum salts thus formed were filtered off and washed with anhydrous ether (20 mL). The filtrate was concentrated on a rotary evaporator to give a yellow solid (138 mg, 83%). This solid was stored either under vacuum or an inert atmosphere: mp 200°–204° C. (dec. determined under vacuum), UV (ethanol) 356 ($\epsilon$=9039), 248 ($\epsilon$=17492); $^1$H NMR (200 MHZ, CDCl$_3$) $\delta$7.94–7.90 (m, 1 H), 7.74 (br, 1 H), 7.30 (d, 1 H, J=9 Hz), 7.14 (m, 1H), 6.19 (d, 1 H, J=8 Hz), 5.54 (d, 1 H, J=8 Hz), 4.38 (s, 2 H), 2.84 (s, 3 H), 2.70 {s, 3H}, 2.52 (s, 3H) , 2.37 (s, 3H); low resolution CIMS m/e (relative intensity) 277 (MH+, 48) , 276 (M+, 100); high resolution CIMS m/e calcd MH+277.1705 found 277.1699.

EXAMPLE 3

This Example illustrates the preparation of $\beta$-Trimethylsilylethyl 2-Carboxymethyl-1,2-dihydroellipticine. Under an atmosphere of argon, degassed anhydrous pyridine (1 mL) was added to a mixture of $\beta$-Trimethylsilylethyl 2-Carboxymethylellipticinium Bromide (5 mg, 0.01 mmol) and polymer supported borohydride (J.C.S. Chem. Comm. 1977, 81.5) (150 mg) and the mixture was stirred at room temperature for 20 hours. The resin was filtered off quickly and washed with benzene (3 mL). The filtrate was concentrated on a rotary evaporator and further dried under high vacuum to give a reddish oil (4 rag): $^1$H NMR (200 MHz, CDCl$_3$) $\delta$8.12 (d, 1 H, J=8 Hz), 7.93 (br s, 1 H), 7.47–7.13 (m*) , 6.22 (d, 1 H, J=8 Hz) , 5.62 (d, 1 H, J=8 Hz), 4.56 (s, 2 H), 4.33–4.24 (m, 2H), 3.80 (s, 2 H), 2.66 (s, 3 H), 2.39 (s, 3 H), 1.10–1.01 (m, 2H), 0.06 (s, 9 H). * it was not possible to integrate this region because of interfering resonances attributed to pyridine.

EXAMPLE 4

This Example illustrates the preparation of 2-(2,3,4-Tri-O-acetyl-$\alpha$-L-arabinosyl )-1,2-dihydroellipticine. This compound was obtained as a yellow oil by using the same procedure used for Example 3 above. $^1$H NMR (200 MHz, CDCl$_3$) $\delta$8.16 (d, 1 H, J=8 Hz), 7.98 (br s, 1 H), 7.47–7.13 (m*), 6.38 (d, 1 H, J=8 Hz), 5.78 (d, 1 H, J=8 Hz), 5.64 (apparent t, 1 H, J=10 Hz), 5.37–5.32 (m, 1H), 5.12 (dd, 1 H, J=10, 3.5 Hz), 4.75 (d, 1 H, J=13 Hz), 4.47 (d, 1 H, J=13 Hz), 4.09 (dd, 1 H, J=13,2 Hz), 3.73 (dd, 1 H, J=13, 1 Hz), 2.75 (s, 3 H), 2.40 (s, 3 H), 2.24 (s, 3 H), 2.03 (s, 3 H), 1.92 (s, 3 H); low resolution CIMS m/e (relative intensity) 507 (MH+, 100), 506 (M+, 82), 259 (23), 247 (72). * it was not possible to integrate this region because of interfering resonances attributed to pyridine.

EXAMPLE 5

This Example illustrates the preparation of 2-Methoxymethyl-1,2-dihydroellipticine. Under an atmosphere of nitrogen, degassed anhydrous pyridine (1 mL) was added to a mixture of 2-methoxymethylellipti-cinium Chloride (5 mg, 0.015 mmol) and excess sodium borohydride and the mixture was stirred at 0° C. for 5 minutes and at room temperature for 30 minutes. The mixture was partitioned between ether (10 mL) and ice water (10 mL). The aqueous layer was extracted once more with ether (10 mL) and the combined organic layers were washed with ice water (5 mL) and dried (MgSO$_4$). The drying agent was filtered off and the filtrate concentrated on a rotary evaporator and dried under high vacuum to give a yellow solid (4.5 mg): $^1$H NMR (200 MHz, CDCl$_3$) δ8.15 (d, 1 H, J=8 Hz), 7.88 (br s, 1 H), 7.44–7.14 (m*, 3 H), 6.37 (d, 1 H, J=8 Hz), 5.58 (d, 1 H, J=8 Hz), 4.65 (s, 2 H), 4.50 (s, 2 H), 3.38 (s, 2 H), 2.71 (s, 3 H), 2.40 (s, 3 H); low resolution CIMS m/e (relative intensity) 293 (MH$^+$, 74), 292 (M$^+$, 99), 261 (45), 247 (100). * integration is approximate because of presence of some resonances attributed to an impurity derived from pyridine.

EXAMPLES 6 and 7

The compounds represented by Formulas VII and XI were prepared for a screening assay as follows:

The screening assay used in Examples 6 and 7 facilitates evaluation by the National Cancer Institute of more than 10,000 new substances per year for cytotoxic and/or growth inhibitory activity against a wide diversity of tumor types and allows the detection of tumor-type-specific sensitivity. Human tumor cell lines, derived from seven cancer types (lung, colon, melanoma, renal, ovarian, brain and leukemia), are selected and developed which are adaptable to a single growth medium and which have reproducible profiles for growth and drug sensitivity. Compounds suspected of having anticancer properties are then tested against these cell lines. The data provided by this in vitro screen indicates those substances which may be effective in vivo against human cancers. This assay is explained more fully in Boyd, "Status of the NCI Preclinical Antitumor Discovery Screen," *Principles & Practice of Oncology*, 3, 1–12 (1989).

The screening assay was performed on 96-well microtitre plates. Relatively high initial inoculation densities were used, in order to permit measurement of "time-zero" values and to enhance the screen's ability to detect and provide some differentiation between anti-proliferative and cytotoxic response parameters. The specific inoculation densities (which range from 500 to 40,000 cells/well) used for each cell line were those which, for the respective line, were determined to give an optical density signal for both the "time-zero" value (at 24 hours) and the "no-drug" control (at 72 hours) above the noise level and within the linear range of the end-point assay (which measures cellular protein). The inoculated microtitre plates were pre-incubated for 24 hours at 37° prior to the addition of compounds represented by Formulas VII and XI.

The dilutions range from $10^{-4}$ to $10^{-8}$ molar. Duplicate wells were prepared for all concentrations; "time-zero" and "no-drug" controls were also provided for each test. The minimum amount of compound required for a 1-time evaluation in the routine screen can be calculated from the knowledge that each test requires a total of approximately 40 ml (0.04 liter) of cell culture medium containing the highest desired drug concentration. Thus, the amount (grams) of sample required (assuming an upper test concentration limit of $10^{-4}$ M) is: molecular weight of compound X $10^{-4} \times 0.04$.

After a 48 hour incubation (37°) with the test compounds, the cells, are fixed in situ to the bottoms of the microtitre wells by addition of 50 μl of either 50% trichloroacetic acid (for adherent cell lines) or 80% trichloroacetic acid (for settled suspension cell lines), followed by incubation for 60 minutes at 4°. The cellular protein in each well is assayed using a sulforhodamine B (SRB) stain procedure. Briefly, after discarding the supernatants, the microtitre plates are washed 5 times with deionized water and air-dried. One hundred microliters of SRB solution (0.4% w/v in 1% acetic acid) is added to each microtitre well and incubated for 10 minutes at room temperature. Unbound SRB is removed by washing 5 times with 1% acetic acid. The plates are air-dried, the bound stain is solubilized with Tris buffer, and the optical densities read at 515 nm. SRB is a bright pink anionic dye which, in dilute acetic acid, binds electrostatically to the basic amino acids of TCA-fixed cells.

Tables I and II present the experimental data collected for the compounds of Formulas VII and XI, respectively, against each cell line. The measured effect, which we term percentage growth (PG), of the compound on a cell line is currently calculated according to one or the other of the following two expressions:

If (Mean OD$_{test}$−Mean OD$_{tzero}$) ≧ 0, then
PG = 100 × (Mean OD$_{test}$ − Mean OD$_{tzero}$)/(Mean OD$_{ctrl}$ − Mean OD$_{tzero}$)

If Mean OD$_{test}$−Mean OD$_{tzero}$ < 0, then
PG = 100 = (Mean OD$_{test}$ − Mean OD$_{tzero}$)/Mean OD$_{tzero}$ Where: Mean OD$_{tzero}$ = The average of optical density measurements of SRB-derived color just before exposure of cells to the test compound (denoted $t_{zero}$). Mean OD$_{test}$ = The average of optical density measurements of SRB-derived color after 48 hrs exposure of cells to the test compound. Mean OD$_{ctrl}$ = the average of optical density measurements of SRB-derived color after 48 hrs with no exposure to the test compound.

On the first two columns of Tables I and II, the sub-panels (e.g., leukemia) and cell lines (e.g., CCRF-CEM) are identified. The next five columns list the calculated PG's for each concentration. The response parameters GI50, TGI, and LC50 are interpolated values representing the concentrations at which the PG is +50, 0, and −50, respectively:

GI50 is the concentration for which the PG = +50. At this value, the increase from time tzero in the number or mass of cells in the test well is only 50% as much as the number or mass of cells in the control well during the period of the corresponding increase in the experiment. A drug effect of this intensity is interpreted as primarily growth inhibitory.

TGI is the concentration for which the PG = 0. At this value, the number or mass of cells in the test well at the end of the experiment equals the number or mass of cells in the well at time $t_{zero}$. A drug effect of this intensity is regarded as cytostasis.

LC50 is the concentration for which the PG = −50. At this value, the number or mass of cells in the test well at the end of the experiment is half that at time $t_{zero}$. This is interpreted as cytotoxicity.

The above response parameters cannot always be obtained by interpolation. If, for instance, all of the PG's in a given row exceed +50, then none of the three parameters can be obtained by interpolation. In such a case, the value given for each response parameter is the highest concentration tested and is preceded by a ">" sign. This practice is extended similarly to the other possible situations where a response parameter cannot be obtained by interpolation.

Tables 1 and 2 indicate that the compounds of Formula VII and XI are effective against many kinds of cancer, and are particularly effective against CNS cancer cell lines. However, the compounds of Formula VII appear to have a somewhat greater effect against CNS cancer lines than those of Formula XI.

TABLE I

| Panel/Cell Line | $\text{Log}_{10}$ Concentration −8.0 | −7.0 | −6.0 | −5.0 | −4.0 | GI50 | TGI | LC-50 |
|---|---|---|---|---|---|---|---|---|
| Leukemia | | | | | | | | |
| CCRF-CEM | 106 | 92 | 78 | 29 | −10 | $3.65 \times 10^{-6}$ | $5.45 \times 10^{-5}$ | $>1.00 \times 10^{-4}$ |
| HL-60 (TB) | 118 | 123 | 121 | 93 | −43 | $2.08 \times 10^{-5}$ | $4.85 \times 10^{-5}$ | $>100 \times 10^{-4}$ |
| K-562 | 105 | 84 | 75 | 11 | −24 | $2.48 \times 10^{-6}$ | $2.04 \times 10^{-5}$ | $>1.00 \times 10^{-4}$ |
| MOLT-4 | 110 | 68 | 30 | 8 | −27 | $3.00 \times 10^{-7}$ | $1.67 \times 10^{-5}$ | $>1.00 \times 10^{-4}$ |
| RPMI-8226 | 104 | 101 | 99 | 38 | −38 | $6.31 \times 10^{-6}$ | $3.15 \times 10^{-5}$ | $>1.00 \times 10^{-4}$ |
| SR | — | — | — | — | — | — | — | — |
| Non-Small Cell Lung Cancer | | | | | | | | |
| A549/ATCC | 102 | 87 | 51 | 10 | −26 | $1.05 \times 10^{-6}$ | $1.92 \times 10^{-5}$ | $>1.00 \times 10^{-4}$ |
| EKVX | 114 | 108 | 43 | 3 | −11 | $7.74 \times 10^{-7}$ | $1.65 \times 10^{-5}$ | $>1.00 \times 10^{-4}$ |
| HOP-18 | 174 | 142 | 121 | 71 | −6 | $1.88 \times 10^{-5}$ | $8.28 \times 10^{-5}$ | $>1.00 \times 10^{-4}$ |
| HOP-62 | 115 | 106 | 14 | −57 | −81 | $4.06 \times 10^{-7}$ | $1.58 \times 10^{-6}$ | $7.89 \times 10^{-6}$ |
| HOP-92 | 121 | 100 | 95 | 37 | −56 | $5.97 \times 10^{-6}$ | $2.51 \times 10^{-5}$ | $8.68 \times 10^{-5}$ |
| NCI-H226 | — | — | — | — | — | — | — | — |
| NCI-H23 | 112 | 97 | 39 | −26 | −48 | $6.48 \times 10^{-7}$ | $4.02 \times 10^{-6}$ | $>1.00 \times 10^{-4}$ |
| NCI-H322M | — | — | — | — | — | — | — | — |
| NCI-H460 | 93 | 85 | 67 | — | −71 | $1.78 \times 10^{-6}$ | $9.40 \times 10^{-6}$ | $4.95 \times 10^{-5}$ |
| NCI-H522 | 97 | 91 | 40 | −30 | −46 | $6.26 \times 10^{-7}$ | $3.71 \times 10^{-6}$ | $>1.00 \times 10^{-4}$ |
| LXFL 529 | 66 | 54 | 14 | −38 | −64 | $1.29 \times 10^{-7}$ | $1.88 \times 10^{-6}$ | $2.91 \times 10^{-5}$ |
| Small Cell Lung Cancer | | | | | | | | |
| DMS 114 | 79 | 64 | 11 | −37 | −46 | $1.83 \times 10^{-7}$ | $1.70 \times 10^{-6}$ | $>1.00 \times 10^{-4}$ |
| DMS 273 | 98 | 77 | 48 | 10 | −72 | $8.27 \times 10^{-7}$ | $1.34 \times 10^{-5}$ | $5.43 \times 10^{-5}$ |
| Colon Cancer | | | | | | | | |
| COLO 205 | 99 | 91 | 63 | −21 | −72 | $1.42 \times 10^{-6}$ | $5.60 \times 10^{-6}$ | $3.71 \times 10^{-5}$ |
| DLD-1 | 103 | 99 | 75 | 26 | −15 | $3.23 \times 10^{-6}$ | $4.23 \times 10^{-5}$ | $>1.00 \times 10^{-4}$ |
| HCC-2998 | 111 | 90 | 98 | 27 | −93 | $4.74 \times 10^{-6}$ | $1.68 \times 10^{-5}$ | $4.39 \times 10^{-5}$ |
| HCT-116 | 106 | 101 | 80 | 29 | −28 | $3.88 \times 10^{-6}$ | $3.22 \times 10^{-5}$ | $>1.00 \times 10^{-4}$ |
| HCT-15 | 118 | 114 | 111 | 96 | 16 | $3.77 \times 10^{-5}$ | $>1.00 \times 10^{-4}$ | $>1.00 \times 10^{-4}$ |
| HT29 | 97 | 112 | 88 | 24 | −73 | $3.92 \times 10^{-6}$ | $1.78 \times 10^{-5}$ | $5.80 \times 10^{-5}$ |
| KM12 | 78 | 59 | 28 | −49 | −86 | $1.94 \times 10^{-7}$ | $2.32 \times 10^{-6}$ | $1.06 \times 10^{-5}$ |
| KM20L2 | 106 | 104 | 82 | 25 | −34 | $3.63 \times 10^{-6}$ | $2.64 \times 10^{-5}$ | $>1.00 \times 10^{-4}$ |
| SW-620 | 89 | 77 | 51 | 18 | −39 | $1.05 \times 10^{-6}$ | $2.04 \times 10^{-5}$ | $>1.00 \times 10^{-4}$ |
| CNS Cancer | | | | | | | | |
| SF-268 | 91 | 76 | 2 | −45 | −55 | $2.23 \times 10^{-7}$ | $1.10 \times 10^{-6}$ | $3.50 \times 10^{-5}$ |
| SF-295 | 88 | 65 | 11 | −30 | −51 | $1.91 \times 10^{-7}$ | $1.89 \times 10^{-6}$ | $8.95 \times 10^{-5}$ |
| SF-539 | 116 | 99 | 30 | −43 | −33 | $5.18 \times 10^{-7}$ | $2.60 \times 10^{-6}$ | $>1.00 \times 10^{-4}$ |
| SNB-19 | 95 | 84 | 16 | 0 | 1 | $3.18 \times 10^{-7}$ | $>1.00 \times 10^{-4}$ | $>1.00 \times 10^{-4}$ |
| SNB-75 | 126 | 86 | −53 | −78 | −58 | $1.81 \times 10^{-7}$ | $4.16 \times 10^{-7}$ | $9.53 \times 10^{-7}$ |
| SNB-78 | 98 | 98 | 41 | −18 | −26 | $6.83 \times 10^{-7}$ | $4.90 \times 10^{-6}$ | $>1.00 \times 10^{-4}$ |
| U251 | 101 | 87 | 3 | −45 | −47 | $2.76 \times 10^{-7}$ | $1.18 \times 10^{-6}$ | $>1.00 \times 10^{-4}$ |
| XF 498 | 174 | 140 | 81 | −25 | −60 | $1.97 \times 10^{-6}$ | $5.82 \times 10^{-6}$ | $5.27 \times 10^{-5}$ |
| Melanoma | | | | | | | | |
| LOX IMVI | 129 | 127 | 119 | 58 | −19 | $1.28 \times 10^{-5}$ | $5.69 \times 10^{-5}$ | $>1.00 \times 10^{-4}$ |
| MALME-3M | 112 | 110 | 55 | −31 | −49 | $1.41 \times 10^{-6}$ | $4.37 \times 10^{-6}$ | $>1.00 \times 10^{-4}$ |
| M14 | 99 | 111 | 103 | 40 | −98 | $7.01 \times 10^{-6}$ | $1.96 \times 10^{-5}$ | $4.52 \times 10^{-5}$ |
| M19-MEL | 117 | 95 | 48 | −36 | −62 | $8.99 \times 10^{-7}$ | $3.70 \times 10^{-6}$ | $3.47 \times 10^{-5}$ |
| SK-MEL-2 | 125 | 137 | 110 | −23 | −91 | $2.83 \times 10^{-6}$ | $6.69 \times 10^{-6}$ | $2.47 \times 10^{-5}$ |
| SK-MEL-28 | 101 | 105 | 91 | 4 | −75 | $2.95 \times 10^{-6}$ | $1.13 \times 10^{-5}$ | $4.86 \times 10^{-5}$ |
| SK-MEL-5 | 99 | 94 | 75 | −53 | −53 | $1.56 \times 10^{-6}$ | $3.85 \times 10^{-6}$ | $9.49 \times 10^{-6}$ |
| UACC-257 | 110 | 113 | 108 | 49 | −5 | $9.63 \times 10^{-6}$ | $8.07 \times 10^{-5}$ | $>1.00 \times 10^{-4}$ |
| UACC−62 | 129 | 118 | 88 | 31 | −44 | $4.68 \times 10^{-6}$ | $2.61 \times 10^{-5}$ | $>1.00 \times 10^{-4}$ |
| Ovarian Cancer | | | | | | | | |
| IGROV1 | 105 | 80 | 47 | 14 | −20 | $8.19 \times 10^{-7}$ | $2.53 \times 10^{-5}$ | $>1.00 \times 10^{-4}$ |
| OVCAR-3 | 98 | 91 | 74 | 10 | −31 | $2.39 \times 10^{-6}$ | $1.73 \times 10^{-5}$ | $>1.00 \times 10^{-4}$ |
| OVCAR-4 | — | — | — | — | — | — | — | — |
| OVCAR-5 | 133 | 136 | 119 | 70 | −10 | $1.78 \times 10^{-5}$ | $7.55 \times 10^{-5}$ | $>1.00 \times 10^{-4}$ |
| OVCAR-8 | 72 | 67 | 28 | 5 | −17 | $2.74 \times 10^{-7}$ | $1.66 \times 10^{-5}$ | $>1.00 \times 10^{-4}$ |
| SK-OV-3 | 192 | 159 | 167 | 148 | −23 | $7.34 \times 10^{-5}$ | $7.34 \times 10^{-5}$ | $>1.00 \times 10^{-4}$ |
| Renal Cancer | | | | | | | | |
| 786-0 | 69 | 38 | 3 | −20 | −56 | $4.08 \times 10^{-8}$ | $1.30 \times 10^{-6}$ | $6.67 \times 10^{-5}$ |
| A498 | 105 | 114 | 93 | 54 | −3 | $1.16 \times 10^{-5}$ | $9.02 \times 10^{-5}$ | $>1.00 \times 10^{-4}$ |
| ACHN | 113 | 113 | 102 | 79 | −4 | $2.24 \times 10^{-5}$ | $8.91 \times 10^{-5}$ | $>1.00 \times 10^{-4}$ |
| CAKI-1 | 110 | 107 | 83 | 38 | −11 | $5.50 \times 10^{-6}$ | $6.07 \times 10^{-5}$ | $>1.00 \times 10^{-4}$ |
| RXF-393 | — | — | — | — | — | — | — | — |
| RXF-631 | 106 | 83 | 38 | 18 | −29 | $5.36 \times 10^{-7}$ | $2.43 \times 10^{-5}$ | $>1.00 \times 10^{-4}$ |
| SN12C | — | — | — | — | — | — | — | — |
| TK-10 | 120 | 127 | 114 | 64 | −6 | $1.59 \times 10^{-5}$ | $8.27 \times 10^{-5}$ | $>1.00 \times 10^{-4}$ |
| UO-31 | 119 | 112 | 101 | 83 | 10 | $2.84 \times 10^{-5}$ | $>1.00 \times 10^{-4}$ | $>1.00 \times 10^{-4}$ |

TABLE II

| Log₁₀ Concentration Panel/Cell Line | Percent Growth in Log₁₀ Concentration | | | | | GI50 | TGI | LC-50 |
|---|---|---|---|---|---|---|---|---|
| | −8.0 | −7.0 | −6.0 | −5.0 | −4.0 | | | |
| Leukemia | | | | | | | | |
| CCRF-CEM | 102 | 94 | 74 | 13 | −35 | $2.48 \times 10^{-6}$ | $1.8 \times 10^{-5}$ | $>1.00 \times 10^{-4}$ |
| HL-60(TB) | 111 | 109 | 102 | 25 | −30 | $4.80 \times 10^{-6}$ | $2.87 \times 10^{-5}$ | $>1.00 \times 10^{-4}$ |
| K-562 | 95 | 83 | 53 | 6 | 2 | $1.17 \times 10^{-6}$ | $>1.00 \times 10^{-4}$ | $>1.00 \times 10^{-4}$ |
| MOLT-4 | 104 | 101 | 68 | 14 | −50 | $2.14 \times 10^{-6}$ | $1.65 \times 10^{-5}$ | $>1.00 \times 10^{-4}$ |
| RPMI-8226 | 109 | 106 | 103 | 39 | −27 | $6.81 \times 10^{-6}$ | $3.93 \times 10^{-5}$ | $>1.00 \times 10^{-4}$ |
| SR | 101 | 86 | 47 | 6 | −42 | $8.46 \times 10^{-7}$ | $1.35 \times 10^{-5}$ | $>1.00 \times 10^{-4}$ |
| Non-Small Cell Lung Cancer | | | | | | | | |
| A549/ATCC | 96 | 86 | 33 | −15 | −66 | $4.69 \times 10^{-7}$ | $4.90 \times 10^{-6}$ | $4.85 \times 10^{-5}$ |
| EKVX | 109 | 114 | 86 | 22 | −22 | $3.60 \times 10^{-6}$ | $3.12 \times 10^{-5}$ | $>1.00 \times 10^{-4}$ |
| HOP-18 | . | . | . | . | . | | | |
| HOP-62 | 121 | 119 | 11 | −39 | −89 | $4.33 \times 10^{-7}$ | $1.64 \times 10^{-6}$ | $1.63 \times 10^{-5}$ |
| HOP-92 | . | . | . | . | . | | | |
| NCI-H226 | 99 | 83 | 19 | −43 | −71 | $3.29 \times 10^{-7}$ | $2.02 \times 10^{-6}$ | $1.74 \times 10^{-5}$ |
| NCI-H23 | 95 | 97 | 42 | −75 | −85 | $6.68 \times 10^{-7}$ | $2.29 \times 10^{-6}$ | $6.15 \times 10^{-6}$ |
| NCI-H322M | 133 | 139 | 99 | 10 | −100 | $3.55 \times 10^{-6}$ | $1.23 \times 10^{-5}$ | $3.51 \times 10^{-5}$ |
| NCI-H460 | 99 | 91 | 78 | 8 | −85 | $2.51 \times 10^{-6}$ | $1.21 \times 10^{-5}$ | $4.21 \times 10^{-5}$ |
| LXFL 529 | 78 | 68 | 35 | −53 | −84 | $3.53 \times 10^{-7}$ | $2.51 \times 10^{-6}$ | $9.23 \times 10^{-6}$ |
| Small Cell Lung Cancer | | | | | | | | |
| DMS 114 | 80 | 73 | 36 | −74 | −68 | $4.14 \times 10^{-7}$ | $2.12 \times 10^{-6}$ | $6.03 \times 10^{-6}$ |
| DMS 273 | . | . | . | . | . | | | |
| Colon Cancer | | | | | | | | |
| COLON 205 | 119 | 92 | 24 | −23 | −28 | $4.16 \times 10^{-7}$ | $3.20 \times 10^{-6}$ | $>1.00 \times 10^{-4}$ |
| DLD-1 | 102 | 93 | 58 | 13 | −69 | $1.48 \times 10^{-6}$ | $1.45 \times 10^{-5}$ | $5.90 \times 10^{-5}$ |
| HCC-2998 | 105 | 108 | 84 | −65 | −91 | $1.69 \times 10^{-6}$ | $3.65 \times 10^{-6}$ | $7.89 \times 10^{-6}$ |
| HCT-116 | 113 | 103 | 83 | 3 | −81 | $2.58 \times 10^{-6}$ | $1.09 \times 10^{-5}$ | $4.28 \times 10^{-5}$ |
| HCT-15 | 111 | 102 | 95 | 76 | −87 | $1.45 \times 10^{-5}$ | $2.93 \times 10^{-5}$ | $5.96 \times 10^{-5}$ |
| HT29 | 99 | 95 | 82 | 4 | −93 | $2.57 \times 10^{-6}$ | $1.11 \times 10^{-5}$ | $3.60 \times 10^{-5}$ |
| KM12 | 97 | 95 | 38 | −48 | −93 | $6.22 \times 10^{-7}$ | $2.78 \times 10^{-6}$ | $1.10 \times 10^{-5}$ |
| KM20L2 | 106 | 95 | 73 | 7 | −91 | $2.22 \times 10^{-6}$ | $1.17 \times 10^{-5}$ | $3.80 \times 10^{-5}$ |
| SW-620 | 89 | 76 | 18 | −21 | −85 | $2.79 \times 10^{-7}$ | $2.87 \times 10^{-6}$ | $2.86 \times 10^{-5}$ |
| CNS Cancer | | | | | | | | |
| SF-268 | 101 | 96 | −39 | −94 | −83 | $2.18 \times 10^{-7}$ | $5.14 \times 10^{-7}$ | $1.60 \times 10^{-6}$ |
| SF-295 | 92 | 87 | 23 | −31 | −91 | $3.81 \times 10^{-7}$ | $2.68 \times 10^{-6}$ | $2.07 \times 10^{-5}$ |
| SF-539 | 99 | 92 | 6 | −58 | −90 | $3.05 \times 10^{-7}$ | $1.23 \times 10^{-6}$ | $7.56 \times 10^{-6}$ |
| SNB-19 | 104 | 97 | 48 | −51 | −57 | $8.97 \times 10^{-7}$ | $3.04 \times 10^{-6}$ | $9.78 \times 10^{-6}$ |
| SNB-75 | 110 | 109 | 20 | −72 | −97 | $4.62 \times 10^{-7}$ | $1.66 \times 10^{-6}$ | $5.75 \times 10^{-6}$ |
| SNB-78 | 131 | 128 | 38 | −33 | −75 | $7.38 \times 10^{-7}$ | $3.41 \times 10^{-6}$ | $2.52 \times 10^{-5}$ |
| U251 | 99 | 89 | 3 | −72 | −87 | $2.86 \times 10^{-7}$ | $1.10 \times 10^{-6}$ | $5.12 \times 10^{-6}$ |
| XF 498 | 101 | 98 | 46 | −33 | −57 | $8.51 \times 10^{-7}$ | $3.84 \times 10^{-6}$ | $5.04 \times 10^{-5}$ |
| Melanoma | | | | | | | | |
| LOX IMVI | 98 | 94 | 82 | 26 | −81 | $3.67 \times 10^{-6}$ | $1.74 \times 10^{-5}$ | $5.14 \times 10^{-5}$ |
| MALME-3M | 113 | 115 | 78 | −40 | −86 | $1.72 \times 10^{-6}$ | $4.58 \times 10^{-6}$ | $1.64 \times 10^{-5}$ |
| M14 | 106 | 94 | 103 | 6 | −93 | $3.52 \times 10^{-6}$ | $1.14 \times 10^{-5}$ | $3.68 \times 10^{-5}$ |
| M19-MEL | 94 | 93 | 38 | −91 | −93 | $6.05 \times 10^{-7}$ | $1.98 \times 10^{-6}$ | $4.83 \times 10^{-6}$ |
| SK-MEL-2 | 98 | 103 | 94 | −92 | −94 | $1.72 \times 10^{-6}$ | $3.20 \times 10^{-6}$ | $5.96 \times 10^{-6}$ |
| SK-MEL-28 | 114 | 115 | 108 | −61 | −95 | $2.21 \times 10^{-6}$ | $4.37 \times 10^{-6}$ | $8.62 \times 10^{-6}$ |
| SK-MEL-5 | 92 | 94 | 77 | −79 | −90 | $1.49 \times 10^{-6}$ | $3.11 \times 10^{-6}$ | $6.49 \times 10^{-6}$ |
| UACC-257 | 97 | 90 | 86 | −8 | −87 | $2.43 \times 10^{-6}$ | $8.23 \times 10^{-6}$ | $3.43 \times 10^{-5}$ |
| UACCO-62 | 106 | 100 | 92 | −91 | −84 | $1.69 \times 10^{-6}$ | $3.18 \times 10^{-6}$ | $5.99 \times 10^{-6}$ |
| Ovarian Cancer | | | | | | | | |
| IGROV1 | 97 | 85 | 30 | −15 | −73 | $4.38 \times 10^{-7}$ | $4.71 \times 10^{-6}$ | $3.99 \times 10^{-5}$ |
| OVCAR-3 | 98 | 94 | 76 | 5 | −91 | $2.34 \times 10^{-6}$ | $1.13 \times 10^{-5}$ | $3.76 \times 10^{-5}$ |
| OVCAR-4 | 113 | 96 | 68 | −6 | −85 | $1.74 \times 10^{-6}$ | $8.34 \times 10^{-6}$ | $3.63 \times 10^{-5}$ |
| OVCAR-5 | 108 | 113 | 97 | 19 | −83 | $3.99 \times 10^{-6}$ | $1.52 \times 10^{-5}$ | $4.74 \times 10^{-5}$ |
| OVCAR-8 | 89 | 81 | 37 | −5 | −95 | $5.16 \times 10^{-7}$ | $7.69 \times 10^{-6}$ | $3.18 \times 10^{-5}$ |
| SK-OV-3 | 87 | 59 | 36 | −16 | −58 | $2.50 \times 10^{-7}$ | $4.87 \times 10^{-6}$ | $6.33 \times 10^{-5}$ |
| Renal Cancer | | | | | | | | |
| 786-0 | 102 | 96 | 32 | 3 | −90 | $5.23 \times 10^{-7}$ | $1.07 \times 10^{-5}$ | $3.73 \times 10^{-5}$ |
| A498 | . | . | . | . | . | | | |
| ACHN | 101 | 96 | 81 | 30 | −92 | $4.02 \times 10^{-6}$ | $1.76 \times 10^{-5}$ | $4.51 \times 10^{-5}$ |
| CAKI-1 | 116 | 106 | 56 | . | −89 | $1.21 \times 10^{-6}$ | $5.89 \times 10^{-6}$ | $2.88 \times 10^{-5}$ |
| RXF-393 | 99 | 96 | 51 | 9 | −92 | $1.04 \times 10^{-6}$ | $1.23 \times 10^{-5}$ | $3.85 \times 10^{-5}$ |
| RXF-631 | 95 | 74 | 30 | −8 | −78 | $3.52 \times 10^{-7}$ | $6.25 \times 10^{-6}$ | $3.95 \times 10^{-5}$ |
| SN12C | 92 | 66 | −36 | −69 | −92 | $1.43 \times 10^{-7}$ | $4.42 \times 10^{-7}$ | $2.65 \times 10^{-6}$ |
| TK-10 | 103 | 101 | 90 | 49 | −93 | $9.46 \times 10^{-6}$ | $2.21 \times 10^{-5}$ | $4.96 \times 10^{-5}$ |
| UO-31 | 103 | 76 | 72 | 36 | −94 | $3.99 \times 10^{-6}$ | $1.88 \times 10^{-5}$ | $4.57 \times 10^{-5}$ |

What is claimed:

1. A compound having the following structure:

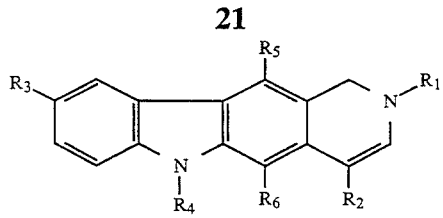

wherein $R_1$ is alkyl having 1 to about 5 carbon atoms, benzyl, alkenyl having 2 to about 5 carbon atoms, alkyloxyalkyl wherein the alkyl portion has 1 to about 5 carbon atoms, hydroxyalkyl having 1 to about 5 carbon atoms, cyanoalkyl having 1 to about 5 carbon atoms, dialkylaminoalkyl wherein each alkyl has 1 to about 5 carbon atoms, glycosyl residue derived from threose, ribose arabinose, xylose, glucose, mannose, galactose, or acetyl derivatives thereof, acids or alkyl esters selected from the group consisting of —$R_7$COOH and —$R_7$COO$R_8$ wherein $R_7$ is an alkyl having 0 to about 4 carbon atoms and $R_8$ is an alkyl having 1 to about 5 carbon atoms;

$R_2$ is hydrogen or formyl;

$R_3$ is hydrogen, alkyl having 1 to about 5 carbon atoms, or acyloxy having 1 to about 5 carbon atoms;

$R_4$ is hydrogen, formyl, alkyl having 1 to about 5 carbon atoms, dialkylaminoalkyl wherein the alkyl portion has 1 to about 5 carbon atoms, morpholino N-alkyl or piperidine N-alkyl, wherein the alkyl has 1 to about 5 carbon atoms; and $R_5$ and $R_6$ are the same or different and are hydrogen or methyl.

2. The compound of claim 1 wherein $R_1$ is an alkyl group.

3. The compound of claim 1 wherein $R_1$ is an alkenyl group.

4. The compound of claim 1 wherein $R_3$ is hydrogen.

5. The compound of claim 1 wherein $R_3$ is an acyloxy group having 1 to about 5 carbon atoms.

6. The compound of claim 1 having the following structure:

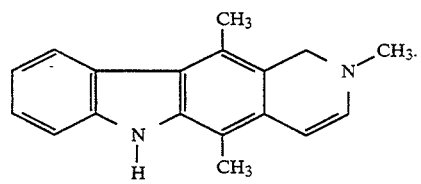

7. The compound of claim 1 having the following structure:

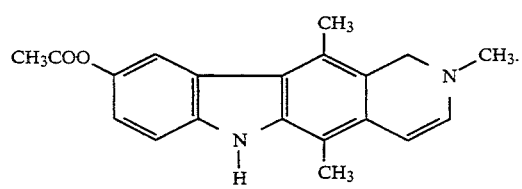

8. The compound of claim 1 having the following structure:

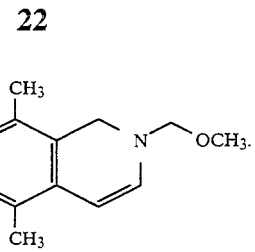

9. The compound of claim 1 having the following structure:

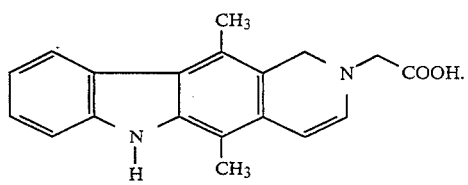

10. The compound of claim 1 having the following structure:

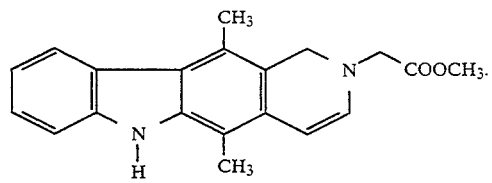

11. The compound of claim 1 having the following structure:

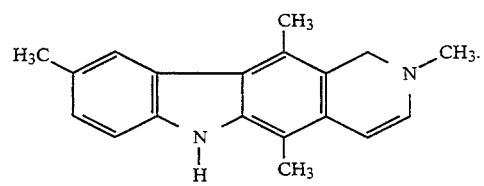

12. The compound of claim 1 having the following structure:

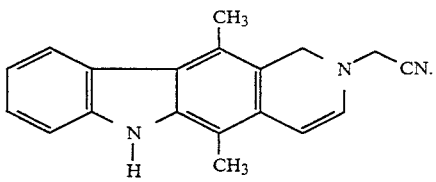

13. The compound of claim 1 having the following structure:

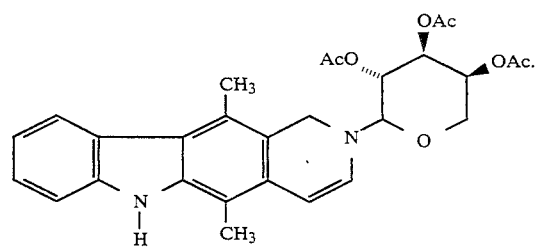

14. The compound of claim 1 having the following structure:

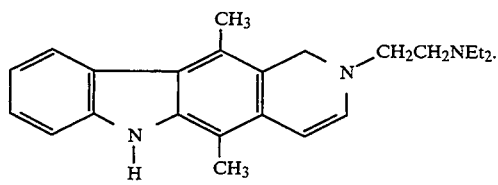

15. The compound of claim 1 having the following structure:

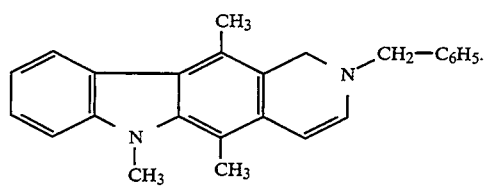

16. The compound of claim 1 having the following structure:

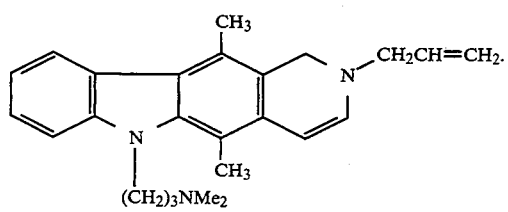

17. The compound of claim 1 having the following structure:

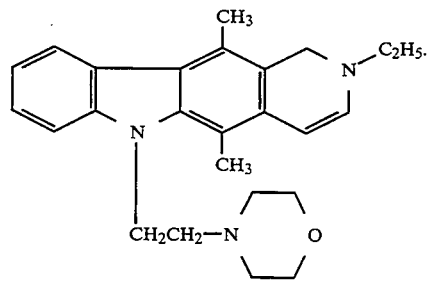

18. The compound of claim 1 having the following structure:

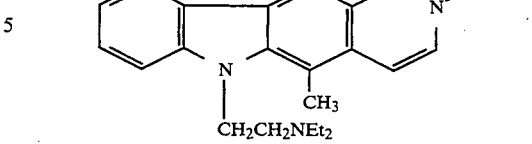

19. The compound of claim 1 having the following structure:

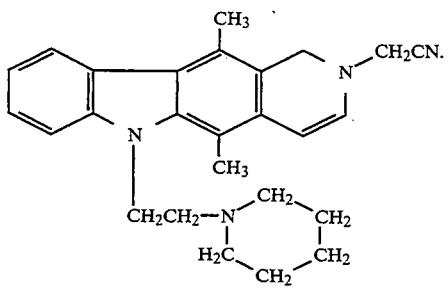

20. The compound of claim 1 having the following structure:

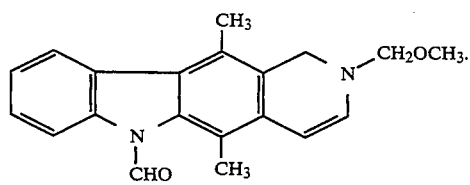

21. The compound of claim 1 having the following structure:

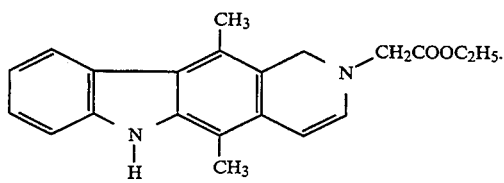

22. A pharmaceutical composition of matter comprising a compound as claimed in claim 1 and a pharmaceutically acceptable carrier therefor.

23. A pharmaceutical composition of matter, in unit dosage form, for use as a CNS anticancer agent, said composition-comprising:
  (i) an amount of a compound as claimed in claim 1 sufficient to release a pharmacologically effective amount of said compound to the brain; and
  (ii) a pharmaceutically acceptable carrier therefor.

24. The compound of claim 1, wherein when $R_4$ is hydrogen, $R_1$ is methyl, and $R_3$ is selected from the group consisting of hydrogen, hydroxy, alkyl having 1 to about 5 carbon atoms or acyloxy having 1 to about 5 carbon atoms.

* * * * *